(12) United States Patent
Ward et al.

(10) Patent No.: US 7,744,544 B2
(45) Date of Patent: Jun. 29, 2010

(54) DERMAL INCISOR

(75) Inventors: Richard D. Ward, Menomonee Falls, WI (US); Samuel W. Huot, Rapid City, SD (US); George F. Dunham, Rapid City, SD (US)

(73) Assignee: Huot Instruments, LLC, Menomonee Falls, WI (US)

( * ) Notice: Subject to any disclaimer, the term of this patent is extended or adjusted under 35 U.S.C. 154(b) by 22 days.

(21) Appl. No.: 11/298,723

(22) Filed: Dec. 9, 2005

(65) Prior Publication Data

US 2007/0135731 A1    Jun. 14, 2007

(51) Int. Cl.
*A61B 10/00*  (2006.01)
*A61B 17/32*  (2006.01)
*A61B 17/14*  (2006.01)

(52) U.S. Cl. .................. 600/567; 600/564; 606/167; 606/184

(58) Field of Classification Search ......... 600/566–567, 600/564; 606/184–185, 167, 180; 30/358, 30/305, 314–315, 347; 83/788, 820, 919
See application file for complete search history.

(56) References Cited

U.S. PATENT DOCUMENTS

| | | | | |
|---|---|---|---|---|
| 2,818,852 A | * | 1/1958 | Kugler | 600/568 |
| 3,026,951 A | * | 3/1962 | Bull | 175/162 |
| 3,990,451 A | | 11/1976 | Gibbs | |
| 4,782,833 A | * | 11/1988 | Einhorn et al. | 606/80 |
| 5,183,053 A | | 2/1993 | Yeh et al. | |
| 5,507,765 A | | 4/1996 | Mott | |
| 5,570,700 A | | 11/1996 | Vogeler | |
| 5,582,041 A | * | 12/1996 | Spiess | 69/37 |
| 6,221,029 B1 | | 4/2001 | Mathis et al. | |
| 2004/0210246 A1 | | 10/2004 | Johanson et al. | |
| 2005/0149076 A1 | | 7/2005 | Borghi et al. | |

FOREIGN PATENT DOCUMENTS

| | | |
|---|---|---|
| DE | 101 19 477 A1 | 10/2002 |
| EP | 0847728 | 7/1998 |
| WO | WO 02/071954 A | 9/2002 |

* cited by examiner

*Primary Examiner*—Max Hindenburg
*Assistant Examiner*—H. Q. Nguyen
(74) *Attorney, Agent, or Firm*—Boyle Fredrickson, S.C.

(57) ABSTRACT

The present invention is a dermal incisor for use in cutting a section from the skin of an individual for examination. The incisor has a housing in which an endless, flexible blade is disposed. The blade is connected to a handle that is rotatable with regard to the housing. Upon rotation of the handle, the blade also rotates in order to cut into the skin. The handle is also slidable with regard to the housing, such that the handle can be used to urge the blade into the skin while being rotated. The housing includes a pair of apertures engaged with a stop pin on the handle to limit the movement of the handle and the blade with respect to the housing in both the horizontal and vertical directions. The housing also includes a lower surface including a number of teeth thereon that securely engages the housing with the skin to prevent slippage of the skin while being cut to provide a smooth incision with few irregularities.

20 Claims, 3 Drawing Sheets

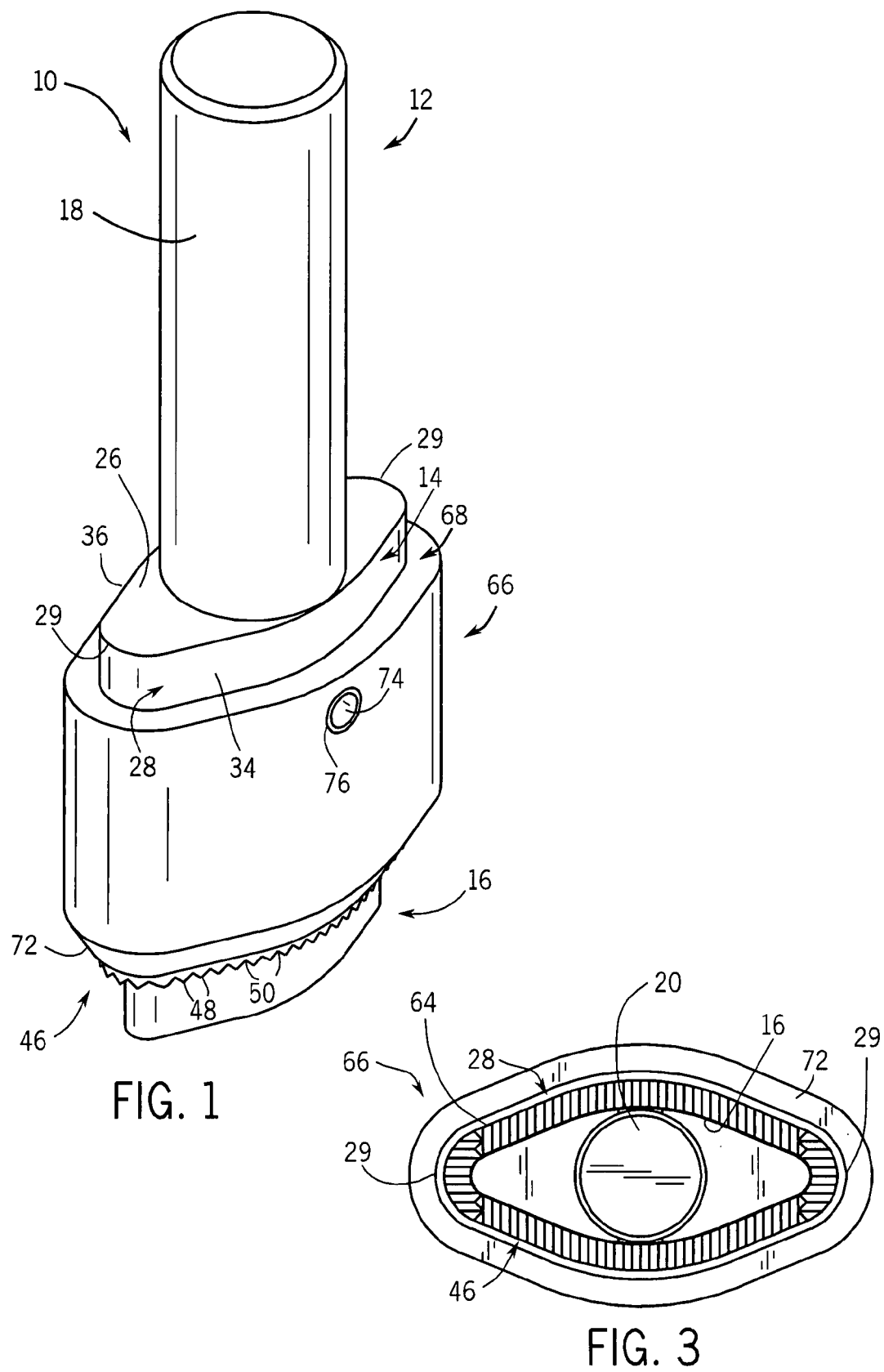

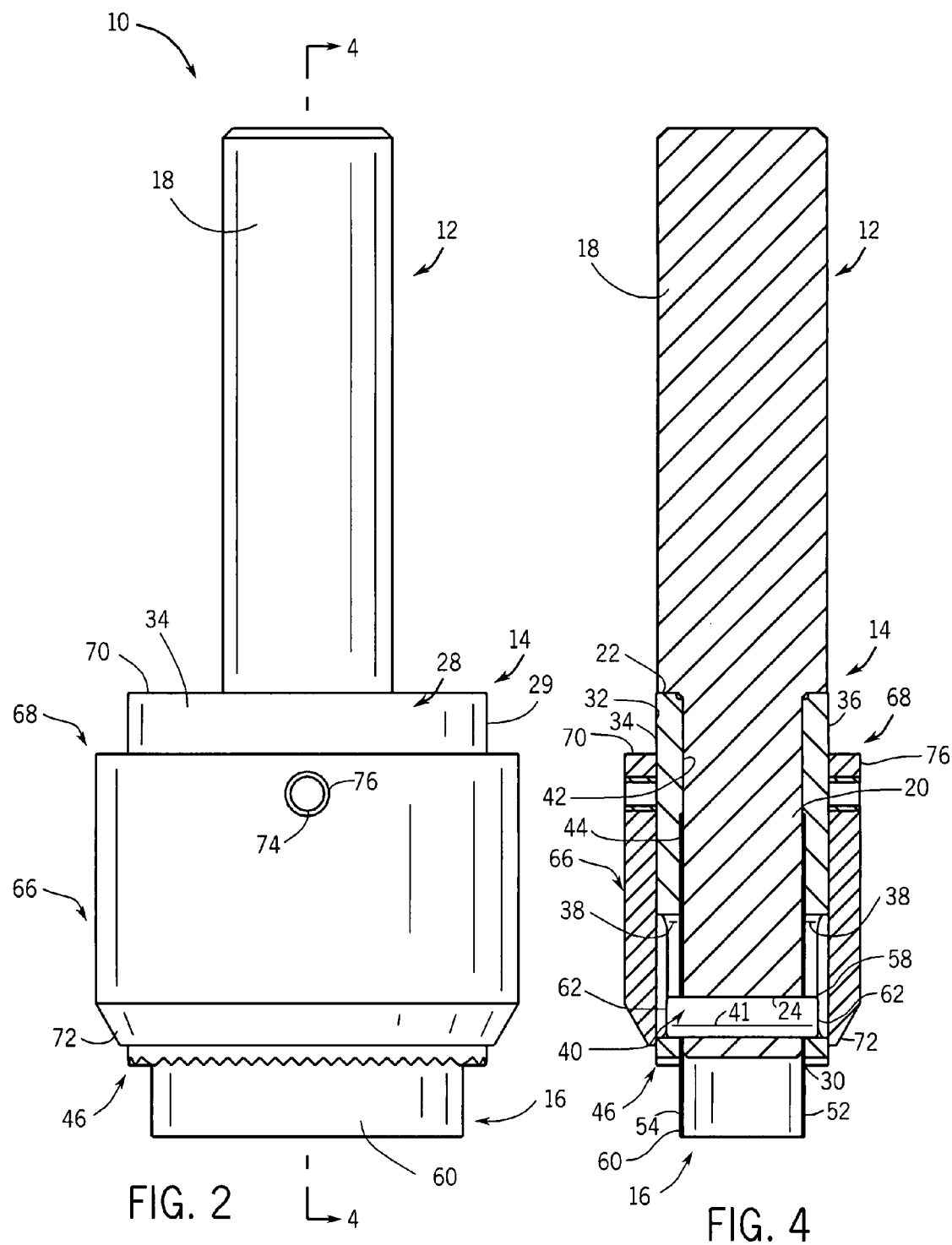

DERMAL INCISOR

FIELD OF THE INVENTION

The invention relates to a punch-type surgical instrument for incising skin in the process of taking a skin specimen for biopsy purposes, or in removing a mole or other skin lesion and part or all of which instrument is disposable, and more particularly to an instrument wherein the blade of the instrument is movable in both the horizontal direction and the vertical direction during use of the instrument.

BACKGROUND OF THE INVENTION

To remove a skin biopsy specimen or to remove a mole or other skin lesion, it is known to incise the skin along a closed line completely penetrating the skin and to then remove the specimen or unwanted skin and tissue containing the lesion by further sharp and blunt dissection, and to thereafter perform a skin closure procedure. It is also known in the incision step to use punch-type instruments having sharp blades which accurately cut closed lines in the skin and which can be held and manipulated by one hand of the surgeon while his or her other hand is used to stretch the skin at the site of the incision. Exemplary instruments of this type are disclosed in U.S. Pat. Nos. 1,577,979; 3,990,541; 5,123,907; 5,183,053; and 5,507,765.

In making a skin incision of the type in question it is usually desirable to have it be of generally elliptical shape. Such an elliptical incision is important for achieving a more suitably appearing skin closure, and is especially beneficial if used while the skin is stretched and held in a cross-grain direction with respect to the skin lines of Langer while the incision is made. U.S. Pat. No. 5,183,053 shows a punch-type surgical instrument for cutting along a generally elliptical closed line, and U.S. Pat. No. 5,123,907 discusses the stretching of the skin relative to the skin's lines of Langer during the incision step.

If an attempt is made to make an elliptical incision free hand using a scalpel and by cutting at different times along two curved incisional lines defining the opposite sides of an ellipse, it is often difficult to make the two incisional lines perfectly symmetrical and therefore the subsequent skin closure, due to several factors, may be irregular. It is also difficult to properly evenly stretch the skin with respect to the lines of Langer while the incision is performed free hand. Therefore, the use of a punch-type instrument to avoid these problems is recommendable.

The amount of skin and adjacent tissue to be removed in the involved surgical procedure will vary from situation to situation, and therefore it is desirable that the punch-type instruments, if used, be available in different sizes so that in each procedure the surgeon will be able to make an incision of a size favorably suiting the biopsy specimen to be taken or lesion to be removed. Further, because of the nature of its use the instrument should be one, which is of relatively inexpensive construction so that it can be used once and then be disposed of.

One exemplary instrument of this type is illustrated in U.S. Pat. No. 5,507,765. The instrument is a punch-type instrument for skin incision, which may be made with a blade having a generally elliptical shape, in which the blade is stably held relative to the handle. This enables the blade to be moved by the handle in various directions without any looseness or slippage between the blade and handle, which can be easily made to cut incisions of different size, and which can be made of a sufficiently low cost as to render it suitably disposable after a single use.

However, with all instruments of this type, because the motion required for making the incision in the skin involves pushing or rocking the blade across the skin to be cut, it is difficult to create a smooth cut, without irregularities that make closure of the incision more difficult, and to control the depth of the incision.

Therefore, it is desirable to develop a dermal incisor that provides an individual with the ability to effectively cut a smooth incision into the skin, while also controlling the depth of the incision. It is also desirable that the instruments have a relatively simple and easy to use construction.

SUMMARY OF THE INVENTION

According to a primary aspect of the present invention, a dermal incisor is provided that is formed as a punch-type surgical instrument for skin incision including a handle, a blade unit separate from the handle, and a housing enclosing portions of both the handle and the blade unit. The blade unit is secured to the handle using a securing means such that the blade unit can move in the vertical direction with respect to the housing in conjunction with the handle. The securing means and the housing structure also enable the handle and blade unit to be rotated with regard to the housing to assist in making a smooth incision in the skin of an individual. The securing means also functions to limit the depth that the blade unit can cut into the skin, enabling a consistent and repeatable incision to be made.

According to another aspect of the present invention, the securing means utilized to connect the handle, the housing and the blade unit can be quickly and easily removed from the instrument to enable the replacement of any dulled or damaged parts of the instrument.

According to a further aspect of the present invention, the housing is formed with a skin-engaging surface adjacent the blade unit that is capable of securely engaging the skin around the blade unit when the instrument is utilized. The skin-engaging surface holds the skin around the blade unit relatively stationary when the blade unit creates the incision in the skin to aid in forming a smooth incision with a minimum of irregularities.

According to still another aspect of the present invention, the blade unit is formed of a durable but flexible material capable of sustaining a cutting edge sufficient to create a smooth incision while being bent due to the rotation of the blade unit with respect to the instrument housing and the skin. The flexibility of the material forming the blade unit enables the blade unit to be used with instrument housings having a number of different configurations to create incisions of different shapes.

Numerous additional aspects, features and advantages of the present invention will be made apparent from the following detailed description taken together with the drawing figures.

BRIEF DESCRIPTION OF THE DRAWINGS

The drawings illustrate the best mode currently contemplated of practicing the present invention.

In the drawings:

FIG. 1 is an isometric view of the dermal incisor constructed according to the present invention;

FIG. 2 is a front plan view of the incisor of FIG. 1;

FIG. 3 is a bottom plan view of the incisor of FIG. 1;

FIG. 4 is a cross-sectional view along line 4-4 of FIG. 2; and

DETAILED DESCRIPTION OF THE INVENTION

Figure 5:
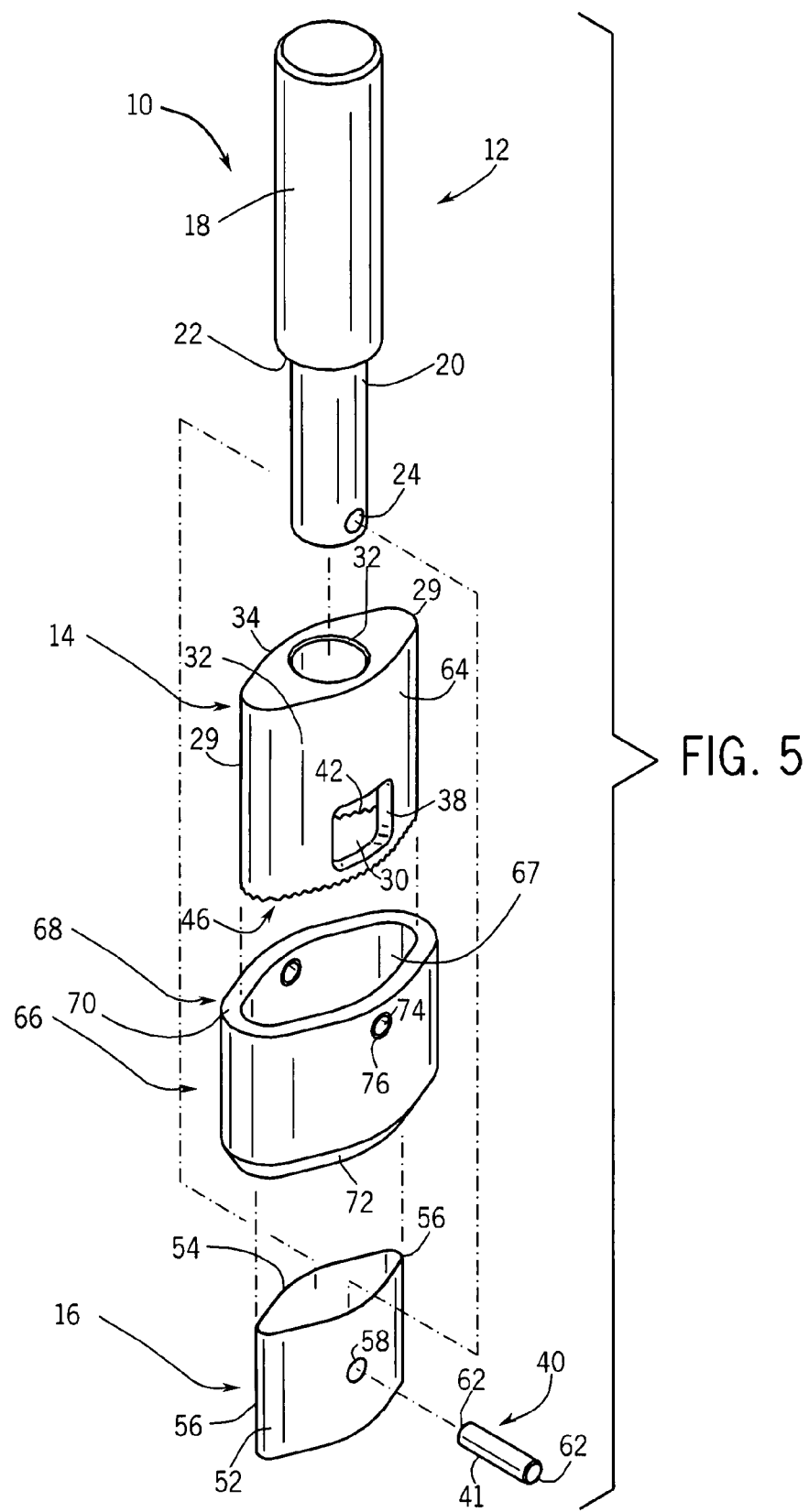
FIG. 5 is an exploded, isometric view of the incisor of FIG. 1.

With reference now to the drawing figures in which like reference numerals designate like parts throughout the disclosure, a dermal incisor constructed according to the present invention is indicated generally at 10 in FIG. 1. The incisor 10 includes a handle 12, and housing 14 and a cutting blade 16.

Referring now to FIGS. 1, 2, 4 and 5, the handle 12 is formed of any suitable material, such as a metal or a plastic, that provides sufficient rigidity to the handle 12 and such that the handle 12 can be cleaned and/or sterilized in a conventional manner to enable the handle 12 to be used repeatedly. The handle 12 includes an upper portion 18 and a lower portion 20 that are preferably integrally formed with one another, depending on the particular material used to form the handle 12, but that can also be separately formed and secured to one another by any suitable means. The upper portion 18 has a diameter that is larger than the diameter of the lower portion 20 in order to form an annular shoulder 22 at the point of intersection of the upper portion 18 and the lower portion 20. The lower portion 20 also includes a bore 24 opposite the upper portion 18 that extends completely through the lower portion 20 generally perpendicular to the longitudinal axis of the handle 12.

The housing 14 is also formed of any suitable material, such as a metal or a plastic, that provides sufficient rigidity to the housing 14 and that can enable the housing 14 to be cleaned and/or sterilized in a conventional manner such that the housing 14 can be used repeatedly along with the handle 12. The housing 14 can have any shape desired in order to form an incision (not shown) of the same shape as the housing 14 when using the incisor 10. In a preferred embodiment, the housing 14 has a diamond-like or elliptical shape as shown in FIG. 1. This shape provides certain advantages with regard to the ability of an individual to create an incision that is easy to close and that leaves a minimal scar upon healing. The housing 14 includes a top wall 26, and a generally continuous side wall 28 with opposed ends 29 that extends downwardly from the periphery of the top wall 26 to define an open lower end 30 opposite the top wall 26. The top wall 26 and the side wall 28 can be formed integrally or separately from one another and subsequently joined to form the housing 14, depending upon the type of material selected for the walls 26 and 28.

The top wall 26 defines a central opening 32 therein. The opening 32 is preferably circular in shape to be complementary to the shape of the lower portion 20 of the handle 12, such that the lower portion 20 can be inserted through the opening 32. Additionally, the diameter of the opening 32 is dimensioned to be slightly larger that the diameter of the lower portion 20 to enable the lower portion 20 to be rotatable within the opening 32.

The side wall 28 includes a pair of opposed sides 34 and 36 that each define an aperture 38 therein. The apertures 38 are configured to have any desired shape, but are preferably generally rectangular or square in shape in order to define the limits of movement for a securing member 40 engageable within each aperture 38. Additionally, the apertures 38 are preferably located adjacent the lower, open end 30 of the housing 14 due the preferred size of the blade 16, but can be positioned anywhere on the sides 34 and 36 of the side wall 28. Also, one or both of the apertures 38 can be formed from alternative structures (not shown) that are located on the interior surface 42 of the side wall 28, such as a notch or recess that extends into the interior surface 42, but does not extend completely through the particular side 34 or 36.

The interior surface 42 of the side wall 28 also defines a recess 44 that extends around the periphery of the side wall 28. The recess 44 extends upwardly from the lower end 30 of the side wall 28 and terminates at a point above each of the apertures 38. The distance of the recess 44 between the lower end 30 and the upper point is sufficient to accommodate the blade 16 with an added amount of space for vertical movement of the blade 16 within the recess 44, in a manner to be described. The depth of the recess 44 in the interior surface 42 of the side wall 28 is formed to be sufficient to accommodate the blade 16 between the side wall 28 and the lower portion 20 of the handle 12. Depending on the thickness of the blade 16 used with the incisor 10, the recess 44 is formed to allow the blade 16 to be inserted into the recess 44 with a small amount of clearance between the side wall 28 on one side and the lower portion 20 on the opposite side, such that the blade 16 can also move in the horizontal direction within the recess 44, in a manner to be described.

To assist in forming the incision in the skin with the incisor 10, as best shown in FIGS. 1-3 and 5, the lower end 30 of the side wall 28 is formed with a skin-engaging surface 46. The surface 46 includes a number of teeth 48 protruding downwardly from the surface 46 along the entire periphery of the surface 46 that are separated by grooves 50. To engage the skin, the teeth 48 are pressed downwardly into the skin to be cut, such that the skin is deformed and urged into the grooves 50 located between the teeth 48. When the incision is made in the skin, the engagement of the teeth 48 and grooves 50 with the skin prevents the skin from shifting with regard to the surface 46, and consequently the housing 14. This facilitates the incision of the skin by the blade 16 in a manner that produces a smooth incision without significant irregularities in the incision.

Looking now at FIGS. 2, 4 and 5, the blade 16 is formed as a generally continuous member with a pair of opposed sides 52 and 54 joined by curved ends 56, and having an overall shape complementary to the shape of the side wall 28. The sides 52 and 54 each define a generally circular opening 58 therein that are aligned with one another. The blade 16 is formed of a suitably rigid, but flexible material in order for the blade 16 to be deformed for insertion into the housing 14. Additionally, when the blade 16 is moved in a horizontal direction in the manner to be described, the blade 16 is continuously engaged and deflected by the interior surface 42 of the side wall 28, necessitating that the material forming the blade 16 is flexible. Suitable materials used to form the blade 16 include various metals including aluminum, titanium, and stainless steel, among others, that can be formed or rolled into thin sheets or strips (not shown). One end or edge of the sheet or strip is then sharpened in a known manner to form the cutting edge 60 for the blade 16, which can have any suitable configuration, such as a serrated blade or wave blade configuration. The sharpened sheets or strips and then be secured to themselves at opposite ends, such as by lap welding, butt welding or spot welding a lapped seam, to form the blade 16. Alternatively, the blade 16 can be formed from an extruded tube of a suitable material to obviate the need to secure opposed ends of the material to one another. When the blade 16 is inserted into the recess 44 defined on the interior surface 42 of the side wall 28, the openings 58 are alignable with the aperture 38 in each side 34 and 36 of the side wall 28 and with the bore 24 in the lower portion 20 of the handle 12.

When aligned with the apertures 38 and bore 24, the openings 58 can slidably receive the securing member 40 therein to affix the blade 16 to the handle 14. The securing member 40 is formed as a generally cylindrical member of a suitably rigid material, such as a metal or hard plastic, having a diameter slightly smaller than the diameters of the bore 24 and openings 58. The securing member 40 also has a length sufficient to enable the opposed ends 62 of the member 40 to extend outwardly from the bore 24 and the openings 58 into the apertures 38 to a position approximately coextensive with the exterior surface 64 of the side wall 28 on each side 34 and 36 of the side wall 28.

In the preferred embodiment, the incisor 10 also includes a shroud 66 positioned around the housing 14. The shroud 66 is formed of a suitable lightweight material, similar to that used to form the handle 12 and the housing 14. The shroud 66 has a cross-sectional shape complementary to the shape of the housing 14, with the interior 67 of the shroud 66 conforming closely to the exterior of the housing 14 to ensure that only a small space is formed between the shroud 66 and housing 14. The shroud 66 has an upper end 68 that forms an annular shoulder 70 with respect to the housing 14, and an inwardly tapering lower end 72. The upper end 68 and shoulder 70 provide a point on the incisor 10 that can easily be grasped by an individual utilizing the incisor 10 to press the incisor 10 downwardly onto the skin to be cut. The lower end 72 is tapered to prevent the shroud 66 from contacting the skin when being pressed upon and forcing the skin away from the housing 14 and blade 16. The shroud 66 can be secured to the exterior of the housing 14 in any suitable manner, but in the illustrated embodiment is affixed to the housing 14 by a pair of set screws 74 inserted through a pair of opposed openings 76 formed in the shroud 66. Alternatively, the screws 74 can be replaced by a snap (not shown) formed by complementary parts on each of the housing 14 and the shroud 66.

The engagement of the securing member 40 with both the lower portion 20 of the handle 14 and with both sides 52 and 54 of the blade 16 allows the handle 12 and blade 16 to move in conjunction with one another when the upper portion 18 of the handle 12 is rotated with respect to the housing 14. The corresponding rotation of the lower portion 20 of the handle 12 is transmitted via the securing member 40 to the sides 52 and 54 of the blade 16, such that the blade 16 is also rotated within the housing 14. As the blade rotates, each side 52 and 54 of the blade 16 contacts and is deflected by the adjacent ends 39 of the side wall 28 towards which the particular side 52 or 54 of the blade 16 is moving. The angular distance that the handle 12 and blade 16 can be rotated is limited by the size and shape of the apertures 38 in the side wall 28. More specifically, because the securing member 40 extends into each of the apertures 38, when the handle 12 is rotated, the securing member 40 is moved towards one edge of each aperture 38. Once the securing member 40 contacts the edge of the aperture 38, the handle 12 and blade 16 are prevented from moving any further in that direction. However, the handle 12 and blade 16 can then be rotated in the opposite direction until the securing member 40 comes into contact with the opposite edge of the apertures 38. This oscillating motion of the handle 12 and blade 16 facilitates the movement of the cutting edge 60 of the blade 16 into and through the skin on which the incisor 10 is positioned. Also, during the oscillating motion of the blade 16, the skin being cut is held securely in position by the skin-engaging surface 46 that is pressed against the skin. This prevents the skin from shifting while being cut, resulting in a smooth incision with a greatly reduced number of irregularities.

In addition to providing a limit on the distance the blade 16 can travel in the horizontal direction, the apertures 38 also limit the distance the blade 16 can travel in the vertical direction. More specifically, due to the size of the recess 44 in the housing 14, the blade 16 can be moved vertically within the housing 14 by sliding the handle 12 towards or away from the housing 14. The movement of the handle 12 and the blade 16 also moves the securing member 40 within each of the apertures 38. The contact of the member 40 with either the upper or lower edge of the apertures 38 provides a limit on the travel of the blade 16 with respect to the housing 14. Preferably, the upper edge of the apertures 38 define a retracted position for the incisor 10, where the cutting edge 60 of the blade 16 is completely disposed within the housing 14, while the lower edge of the apertures 38 define an extended position where the cutting edge 60 is spaced a distance from the lower end 30 of the housing 14 equal to a maximum depth for the incision to be made in the skin being cut. The extended position can also be redundantly set by the location of the annular shoulder 22 on the handle 12 and its corresponding engagement with the top wall 26 of the housing 14.

In addition to the above-described preferred embodiment, other variations of the incisor 10 are also possible. For example, the blade 16, instead of being positioned within the housing 14, can be disposed around the exterior surface 64 of the housing 14, with the securing member 40 extending past the exterior surface 64 into engagement with the openings 58 in the blade 16. Also, instead of the pin 41, the securing member 40 can be formed of other structures or mechanisms, such as a gear drive (not shown) disposed on the lower portion 20 of the handle 12 and engaged with a complementary toothed structure located on the interior of the blade 16. By rotating the handle 12, the gear-like structure will also rotate and move the blade 16 due the engagement of the gear-like structure with the toothed structure on the blade 16. As another alternative structure, the securing member 40 can take the form of a friction drive mechanism (not shown) that directly engages the blade 16 using frictional forces that operate to move the blade 16 in conjunction with the handle 12. Further, the vertical movement of the blade 16 within the housing 14 can be omitted entirely, or controlled by a mechanism other than the handle 12, such as a selectively operated, spring-biased mechanism positioned between the housing 14 and the blade 16.

Various other embodiments of the present invention are contemplated as being within the scope of the following claims particularly pointing out and distinctly claiming the subject matter regarded as the invention.

We hereby claim:

1. A medical manually-operated punch-type cutting tool comprising:
   a) a housing with a non-circular cross section;
   b) a handle rotatably connected to the housing; and
   c) an endless, flexible blade engaged with the housing opposite the handle and conformable to the cross-sectional shape of the housing configured to punch a non-circular cut as defined by the cross-sectional shape of the housing, the blade operably connected to the handle for rotation therewith, wherein as the blade is rotated by rotating the handle with respect to the housing, the blade is continuously in contact with and deflected by an interior surface of the housing to conform to the cross-sectional shape of the housing as a result of contact between the blade and the interior surface of the housing when in contact with a skin substrate to cut a non-circular opening within the skin substrate, the cut opening corresponding to the shape of the endless blade as it conforms to the cross-sectional shape of the housing.

2. The tool of claim 1 wherein the housing defines a longitudinal axis and the handle is rotatable with respect to the longitudinal axis of the housing.

3. The tool of claim 2 wherein the handle and the blade are slidable with respect to the longitudinal axis of the housing.

4. The tool of claim 3 wherein the blade is slidable between a retracted position where a cutting edge of the blade overlaps the housing, and an extended position where the cutting edge blade is spaced from the housing.

5. The tool of claim 2 further comprising a movement limiting mechanism engaged between the handle and the housing.

6. The tool of claim 4 wherein the movement limiting mechanism comprises a pin with a central portion extending through the handle and at least one end positioned within an aperture in the housing.

7. The tool of claim 6 wherein the at least one end of the pin extends through an aperture disposed in the blade.

8. The tool of claim 1 wherein the blade is disposed within the housing.

9. The tool of claim 1 further comprising a shroud secured around the housing.

10. The tool of claim 1 wherein the housing includes a substrate-engaging surface disposed opposite the handle.

11. A punch-type surgical incision instrument comprising:
a) a housing with a non-circular cross section and including a top wall defining an opening therein and a peripheral side wall;
b) a handle rotatably connected to the housing and having an upper portion and a lower portion, the lower portion extending through the opening in the top wall;
c) a movement limiting member connected to the lower portion of the handle and engaged with the housing to control the movement of the handle with regard to the housing; and
d) a flexible blade having a generally non-circular cross section engaged with the housing opposite the top wall and conformable to the cross-sectional shape of the housing, the blade configured to punch a non-circular cut as defined by the cross-sectional shape of the housing, the blade also connected to the movement limiting member for rotation with the movement limiting member and the handle, wherein as a result of contact between the blade and the side wall of the housing as the blade is rotated by rotating the handle with respect to the housing, the blade is continuously in contact with and deflected by an interior surface of the side wall of the housing to conform to the non-circular cross-sectional shape of the housing when in contact with a skin substrate to cut a non-circular opening within the skin substrate, the cut opening corresponding to the shape of the flexible blade as it conforms to the cross-sectional shape of the housing.

12. The instrument of claim 11 wherein the lower portion of the handle and the blade are slidable with respect to the housing.

13. The instrument of claim 12 wherein the movement limiting mechanism comprises:
a) a stop member connected between the lower portion of the handle and the blade, the stop member having a pair of opposed ends; and
b) a pair of apertures disposed on opposite sides of the housing, wherein the opposed ends of the stop member are movably positioned within the apertures to selectively engage the perimeter of the pair of apertures.

14. The instrument of claim 13 wherein the pair of apertures are generally square in shape.

15. A method for creating a surgical incision in a skin substrate, the method comprising the steps of:
a) providing a medical punch-type cutting tool including a housing with a non-circular cross section, a handle rotatably connected to the housing, and an endless, flexible blade engaged with the housing opposite the handle and conformable to the cross-sectional shape of the housing configured to punch a non-circular cut as defined by the cross-sectional shape of the housing, the blade operably connected to the handle for rotation therewith;
b) placing the tool against the skin substrate; and
c) rotating the handle with respect to the housing to rotate the blade against and cut the substrate, wherein as a result of contact between the blade and an interior surface of the housing, the blade is continuously in contact with and deflected by the interior surface of the housing to conform to the non-circular cross-sectional shape of the housing when in contact with the skin substrate to cut a non-circular opening within the substrate, the cut opening corresponding to the shape of the endless blade as it conforms to the cross-sectional shape of the housing.

16. The method of claim 15 further comprising the step of sliding the handle into the housing to urge the blade into the substrate simultaneously with rotating the handle.

17. The method of claim 15 wherein the step of rotating the handle comprises the steps of:
a) rotating the handle in one of a clockwise or counterclockwise direction; and
b) rotating the handle in the other of the clockwise or counterclockwise direction.

18. The method of claim 17 wherein the tool includes a movement limiting member connected to handle and engaged with the housing, and wherein the step of rotating the handle comprises the steps of:
a) rotating the handle in one of a clockwise or counterclockwise direction until the movement limiting mechanism prevents further movement of the handle; and
b) rotating the handle in the other of the clockwise or counterclockwise direction until the movement limiting mechanism prevents further movement of the handle.

19. The method of claim 15 wherein the step of placing the tool against the substrate comprises contacting the substrate with a substrate-engaging surface on the housing opposite the handle.

20. A punch-type surgical incision instrument comprising:
a) a housing with a non-circular cross section and including a top wall defining an opening therein and a peripheral side wall having an interior surface;
b) a handle rotatably connected to the housing and having an upper portion and a lower portion, the lower portion extending through the opening in the top wall;
c) an endless, flexible blade engaged with the interior surface of the peripheral side wall of the housing opposite the top wall and conformable to the cross-sectional shape of the housing, the blade configured to punch a non-circular cut as defined by the cross-sectional shape of the housing, the blade also connected to the handle for rotation with the handle, wherein as the blade is rotated by rotating the handle with respect to the housing, the blade is continuously contacted and deflected by the interior surface of the side wall of the housing to conform to the non-circular cross-sectional shape of the housing while in contact with a skin substrate to form an incision;
d) a movement limiting member fixed between the lower portion of the handle and the blade, and engaged opposite the handle with the housing to control the movement of the handle and the blade in both a horizontal and a vertical direction with regard to the housing while the blade is in contact with the skin substrate in which a non-circular incision is to be formed by the blade, the incision corresponding to the shape of the endless blade as it conforms to the cross-sectional shape of the housing.

* * * * *